United States Patent [19]

Pandey

[11] Patent Number: 5,159,002

[45] Date of Patent: Oct. 27, 1992

[54] METHOD FOR PURIFYING DERMOSTATIN A AND DERMOSTATIN B

[75] Inventor: Ramesh C. Pandey, Libertyville, Ill.

[73] Assignee: Xechem Inc., New Brunswick, N.J.

[21] Appl. No.: 475,140

[22] Filed: Feb. 2, 1990

[51] Int. Cl.⁵ ............................................ C07D 313/00
[52] U.S. Cl. .................................................... 549/271
[58] Field of Search ......................... 549/271; 519/450

[56] References Cited

U.S. PATENT DOCUMENTS

| | | | |
|---|---|---|---|
| 4,743,695 | 5/1988 | Schmitz et al. | 549/271 |
| 4,863,955 | 9/1989 | Moore et al. | 549/271 |

OTHER PUBLICATIONS

R. Pandey et al., *The Journal of Antibiotics*, "Polyene Antibiotics," vol. XXVI, No. 8 pp. 475-477 (1973).

R. Pandey, *Hindustan Antibiotics Bulletin*, "The Structures of Dermostatin A and B," 22 (3 & 4), pp. 47-61 (1980).

H. Willard et al., "Instrumental Methods of Analysis" 6th ed., pp. 529-530 and 536-543, D. Van Nostrand Co. New York (1981).

N. Narasimhachari et al., *Chemical Abstracts* 65:5301c, "Purification of dermostatin . . . " (1965).

M. Windholz et al., "The Merck Index" 10th ed. entry 2280, p. 420, Merck & Co., Rahway, N.J. (1983).

R. Pandey et al., *Chemical Abstracts* 79:146360v, "Polyene Antibiotics," p. 311 (1973).

*Primary Examiner*—Richard L. Raymond
*Assistant Examiner*—Mark W. Russell
*Attorney, Agent, or Firm*—W. Dennis Drehkoff

[57] ABSTRACT

The present invention provides a method for treating patients suffering from the acquired immunedeficiency syndrome (AIDS). The method comprises administering dermostatin, dermostatin A, dermostatin B or derivatives thereof, such as pharmaceutically acceptable esters, salts or complexes. The administration of the dermostatin or dermostatin A or dermostatin B should be done as soon as possible after the detection of the presence of the HIV virus which is believed to be responsible for the onset of AIDS. These polyene macrolide antibiotics have been found to be effective in improving the viability of lumphocyte cells infected with the HIV virus and in preventing the replication of the virus. The present invention also provides for the first time substantially pure dermostatin A and dermostatin B and an HPLC method for separation of dermostatin complex into those components in substantial purity.

1 Claim, 11 Drawing Sheets

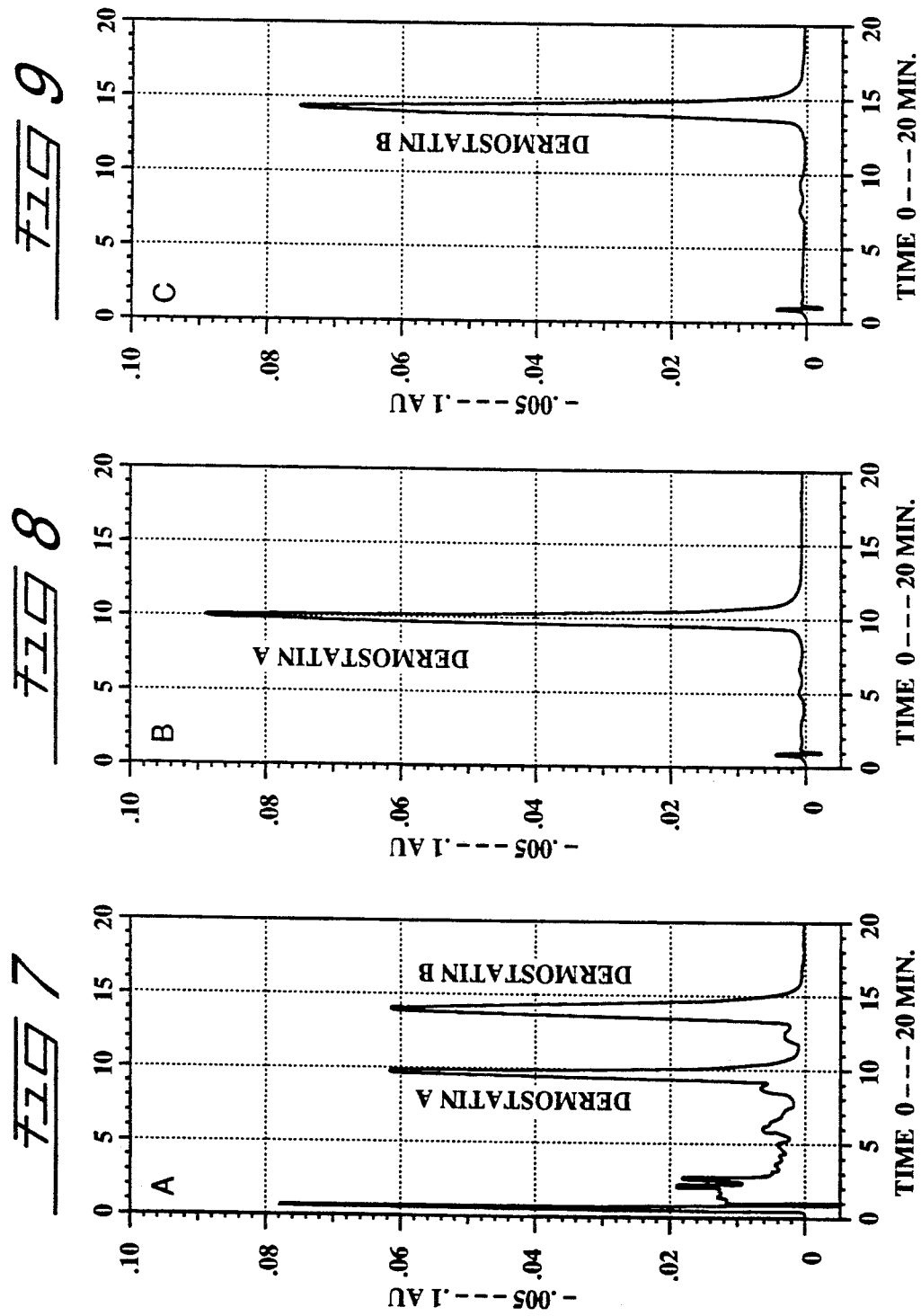

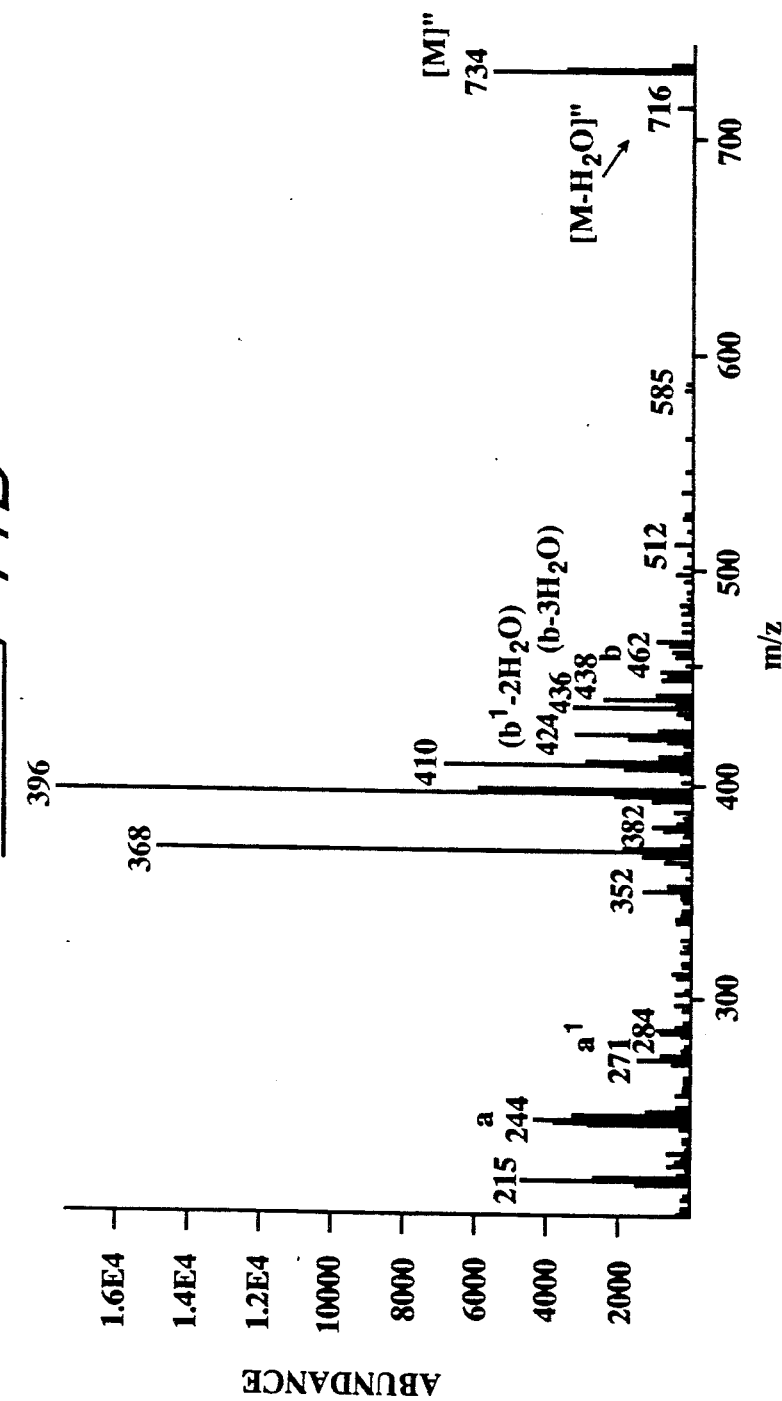

_FIG. 12_
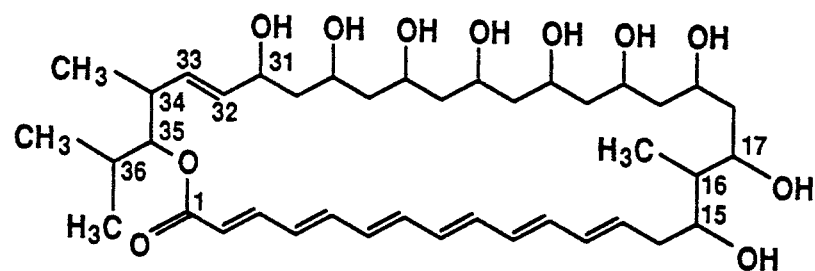
_FIG. 13_
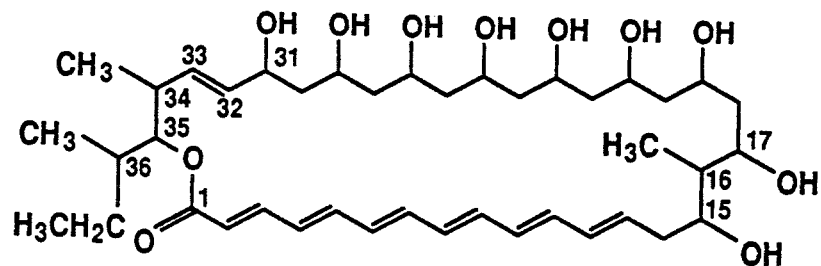

METHOD FOR PURIFYING DERMOSTATIN A AND DERMOSTATIN B

FIELD OF THE INVENTION

This invention relates generally to the field of pharmacology and more specifically to chemotherapeutic compositions and methods for treating the acquired immunodeficiency syndrome (AIDS).

BACKGROUND OF THE INVENTION

AIDS has been as puzzling to researchers as it has been devastating to the infected population.

AIDS is a contagious disease that destroys the body's ability to fight infection, and is transmitted through blood and other bodily fluids—mainly during sexual intercourse. An individual may contract AIDS from an AIDS carrier who is not suffering from the illness and may even be unaware of the infection. There is no known cure for AIDS and sufferers typically die within three years of contracting the disease. While reports of promising anti-AIDS drugs surface frequently, test results have so far been disappointing. One drug after receiving much attention was proven ineffective, if not actually harmful.

Although many drugs have shown promise against AIDS, none have been shown to be capable of curing AIDS once it has been contracted. Amer. Pharm. NS 26-36 (Jan.) 1986, Amer. Pharm. NS 25:14 (July) 1986. Similarly, prospects for an AIDS vaccine have been found to be poor. Most estimates have been that it will take researchers ten years to devise a way to immunize high-risk groups. Meanwhile, the disease continues to spread at an alarming rate. Although the etiology of AIDS is poorly understood the symptomology is similar to other immune system anomalies.

Primary immunodeficiency is a rare, but devastating, condition in which there is a partial or total collapse or absence of one or more classes of immune responses. It is typified by recurrent or chronic life-threatening infections and by the necessity for its victims to live in rigorously controlled, sterile conditions. There is no existing treatment other than isolation of the patient from all potential sources of infection.

Secondary immunodeficiency, in which the immune system function is reduced, may appear as a result of age, disease or the use of certain therapies, such as cytostatic radiotherapy or chemotherapy for cancer. Patients whose immune system function is reduced are vulnerable to both viral and other infections, and treatment of such infections may be complicated and/or protracted.

Acquired immune deficiency syndrome (AIDS) is a recently identified syndrome in which a person's immune system after functioning normally ceases to function adequately. While AIDS resembles somewhat the clinical pathology of secondary immunodeficiency, it alone is uniquely characterized by a reduced ratio of helper to suppressor T-cell subsets, as explained below.

Because of the breakdown in the immune system, individuals suffering from AIDS are highly vulnerable to infections resulting in a high mortality from opportunistic infections and Kaposi's sarcoma. See, e.g. "Immunocompromised Homosexuals" (Editorial) Lancet 1981; ii: 1325-6; Center for Disease Control, "Epidemiological Aspects of the Current Outbreak of Kaposi's Sarcoma and Opportunistic Infections", N. Engl. J. Med. 1982, 306: 248-52; Gerstoft et al., "Severe Acquired Immunodeficiency in European Homosexual Men", Br. Med. J. 1982, 285: 17-19. The two year mortality rate has been reported to be as high as 80%.

The etiology of AIDS is ascribed to a human T-lymphotropic retrovirus (HTLV or LAV, or human immunopathic virus [HIV]) the discovery of which has stimulated an active search for effective anti-retroviral chemotherapeutic agents. As yet no agents have been shown to be truly effective in curing HIV infection or reversing the underlying immunodeficiency.

To understand the hypothesized effect of the HIV virus on the human body, it is first necessary to have a basic understanding of the body's normal immune system. The human body's mechanisms for responding to invading infectious organisms are extremely complex. The principal immune reaction depends upon cells, called lymphocytes, which recognize the need for, and initiate, appropriate responses. Lymphocytes are broadly classified into two groups, B and T cells, and in turn both groups are further categorized into a diversity of types or subsets, especially the T cells.

Functionally, there are two kinds of T cells, effector T cells, which cause various immune reactions and regulatory T cells which control the development of effector lymphocytes, both of the T and B type. The regulatory T cells may also be broken into three subsets, T regulatory, T helper, and T suppressor cells. The T helper cells stimulate the proliferation of B cells and T effector cells which are responsible for directly combating infection, whereas T suppressor cells block the effect of the T helper cells.

In a human with normal immune responses, the ratio of T helper cells to T suppressor cells is approximately 2:1. However, uniquely, in a patient suffering from AIDS, the ratio of T helper cells to T suppressor cells is substantially reduced, usually to a point at which the number of T suppressor cells exceeds the number of T helper cells. The exact reason for this phenomenon is not known. However, it has been found that the HIV virus specifically invades and destroys T helper cells.

HIV is an RNA retrovirus. Other known retroviruses induce sarcomas, leukemias, lymphomas, and mammary carcinomas in animals. The unique aspect of a retrovirus is that it reproduces through a DNA intermediate. The progeny RNA is then generated through regular transcription of the DNA intermediate. The DNA intermediate is produced via a polymeric enzyme called reverse transcriptase. Thus, the fact that HIV is a retrovirus can be confirmed by the presence of the viral reverse transcriptase.

The fact that the HIV virus is present within a host can also be determined by analyzing for the presence of the viral protein antigens p24 and p17. The presence of such antigens in cells indicates the presence of the HIV virus.

Dermostatin and dermostatin A and dermostatin B are carbonyl conjugated polyene macrolide antimicrobial agents. Dermostatin complex which contains both dermostatin A and dermostatin B has been used as an effective agent for the treatment of fungal infections in humans. Heretofore, dermostatin A and dermostatin B have not been isolated and separated from the dermostatin complex. Amphotericin B is the drug of choice for many systemic fungal infections in humans for many years. The antifungal activity of amphotericin B is at least in part dependent upon its binding to a sterol moiety in the cell membrane. By virtue of this interaction, channels, or pores are formed in the cell membrane allowing leakage of a variety of small molecules. However, effects of amphotericin B on the permeability of sterol-free membranes have suggested that additional mechanisms may be involved.

Other polyene antibiotics, such as nystatin, natamycin, hamycin, aureofungin and candicidin, have been known and used clinically for many years. More recently, dermostatin has been found to have activity against fungi and to be useful in the treatment of certain fungal infections.

SUMMARY OF THE INVENTION

It has now been discovered that dermostatin A, dermostatin B and their derivatives, including their pharmaceutically acceptable salts, esters and complexes can be employed to effectively treat AIDS. The reasons for the effectiveness of dermostatin A, dermostatin B and their derivatives are not well understood. However, one aspect of their use which appears to be beneficial is the employment of treatment prior to extensive development of the HIV virus within the host.

Dermostatin A and dermostatin B have been found to improve the viability of lymphocyte cells in the presence of HIV and to inhibit the ability of the HIV virus to replicate within the lymphocyte after penetration by the virus. Also, in accordance with the present invention, dermostatin has been separated into its constituents dermostatin A and dermostatin B for the first time, using preparative high performance liquid chromatography.

BRIEF DESCRIPTION OF THE FIGURES

FIG. 7 is a high performance liquid chromatogram for dermostatin complex.

FIG. 8 is a high performance liquid chromatogram for dermostatin A.

FIG. 9 is a high performance liquid chromatogram for dermostatin B.

FIG. 12 is the structural formula for dermostatin A.
FIG. 13 is the structural formula for dermostatin B.

DETAILED DESCRIPTION OF THE PREFERRED EMBODIMENTS

As indicated, in accordance with the present invention, dermostatin (also known as dermostatin complex) which contains both dermostatin A and dermostatin B has been separated into its components to produce high-purity dermostatin A and dermostatin B, which heretofore has not been available. The dermostatin complex is separated by use of a specific separation procedure which comprises dissolving the dermostatin complex in dimethylsulfoxide (DMSO) at any suitable concentration, such as from about 1 to about 100 mg dermostatin per milliliter of DMSO, preferably about 20 mg/ml. The solution is then injected, in aliquots, into a suitable separation column, using an isocratic solvent system of methanol-water as the mobile phase. The methanol-water ratio may range from about 60 parts of methanol per 40 parts of water to about 80 parts of methanol per 20 parts of water. Preferably, the methanol-water ratio is about 74:26. A typical flow rate of from about 10 to about 20 ml per minute is suitable, about 14 ml per minute being preferred. The detection for the elution of each component is followed at 390 nm and as the peak is detected, 50 ml or other suitably sized fractions are collected. The fractions are then analyzed to identify the fractions which are dermostatin A and dermostatin B, respectively. The fractions with identical retention times are then combined and concentrated, as by rotary evaporation, and the resulting precipitate is filtered and dried. When using a Waters Delta Pak $C_{18}$ column (19×300 mm, 100 angstrom, 15 micron particle size) the fraction having a retention time of 9.92 minutes is the dermostatin A fraction and the fraction having a retention time of 14.36 minutes is the dermostatin B fraction.

Figure 1:
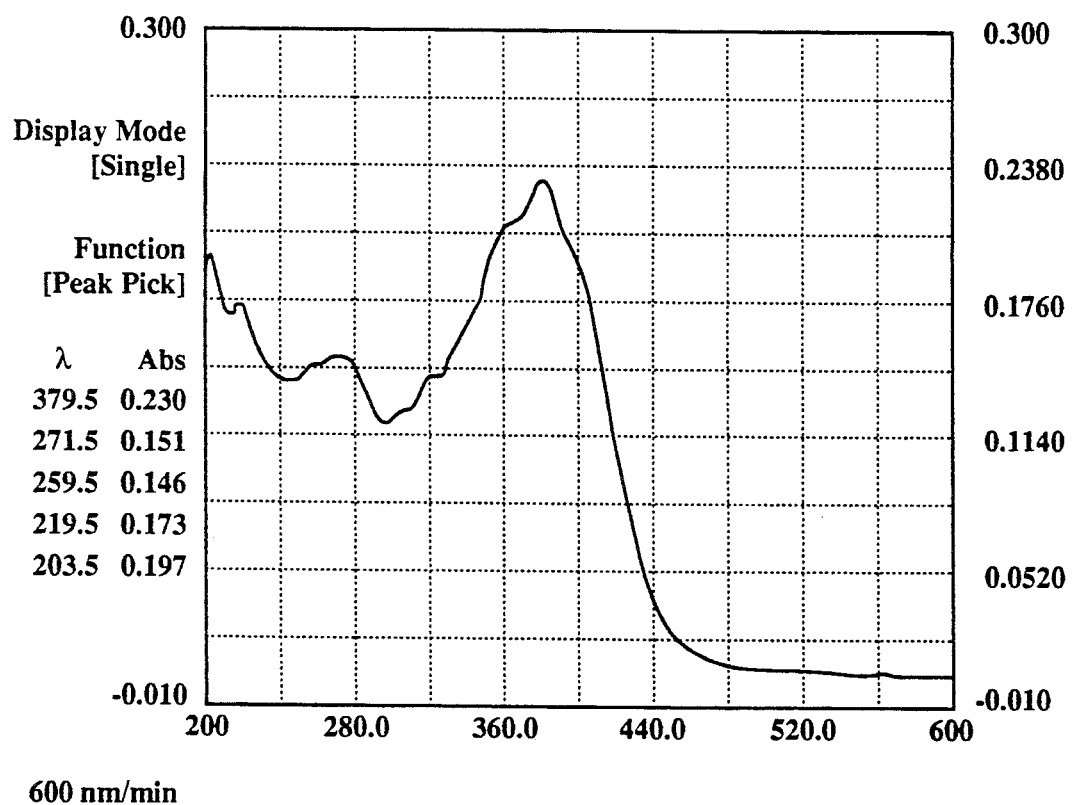
FIG. 1 is a plot of the ultraviolet-visible spectrum for dermostatin complex in methanol.
Figure 2:
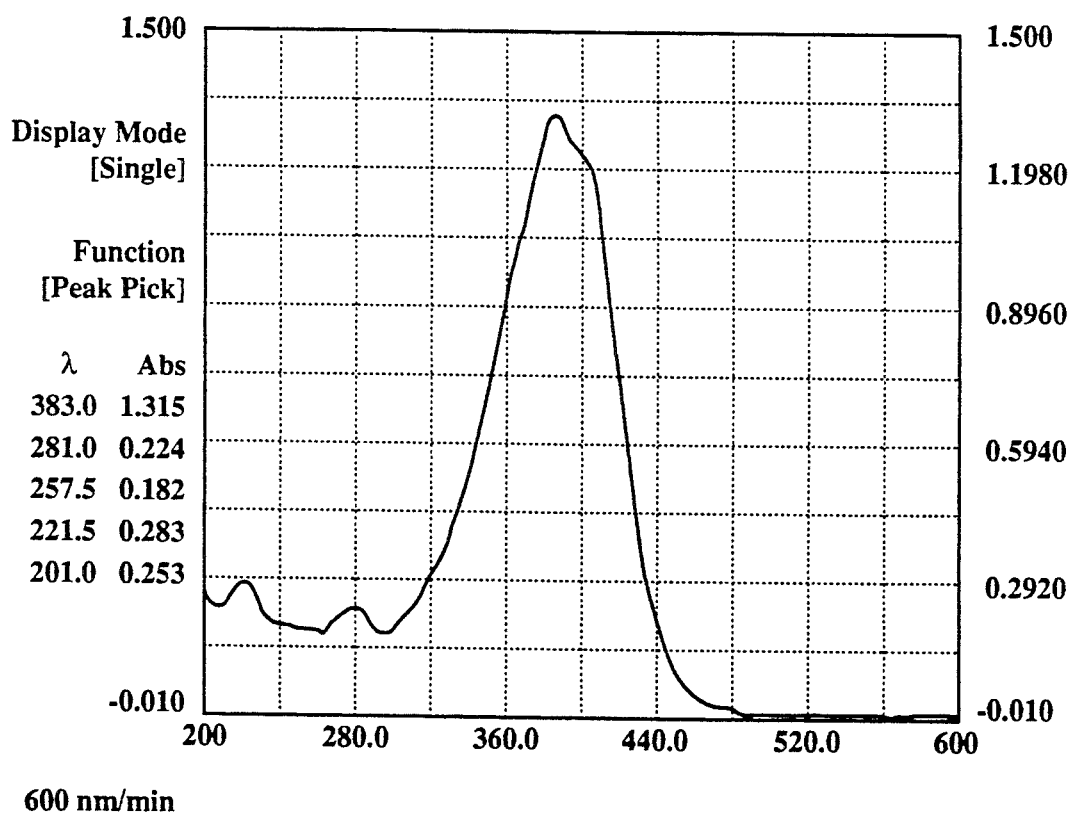
FIG. 2 is a plot of the ultraviolet-visible spectrum for dermostatin A in methanol.
Figure 3:
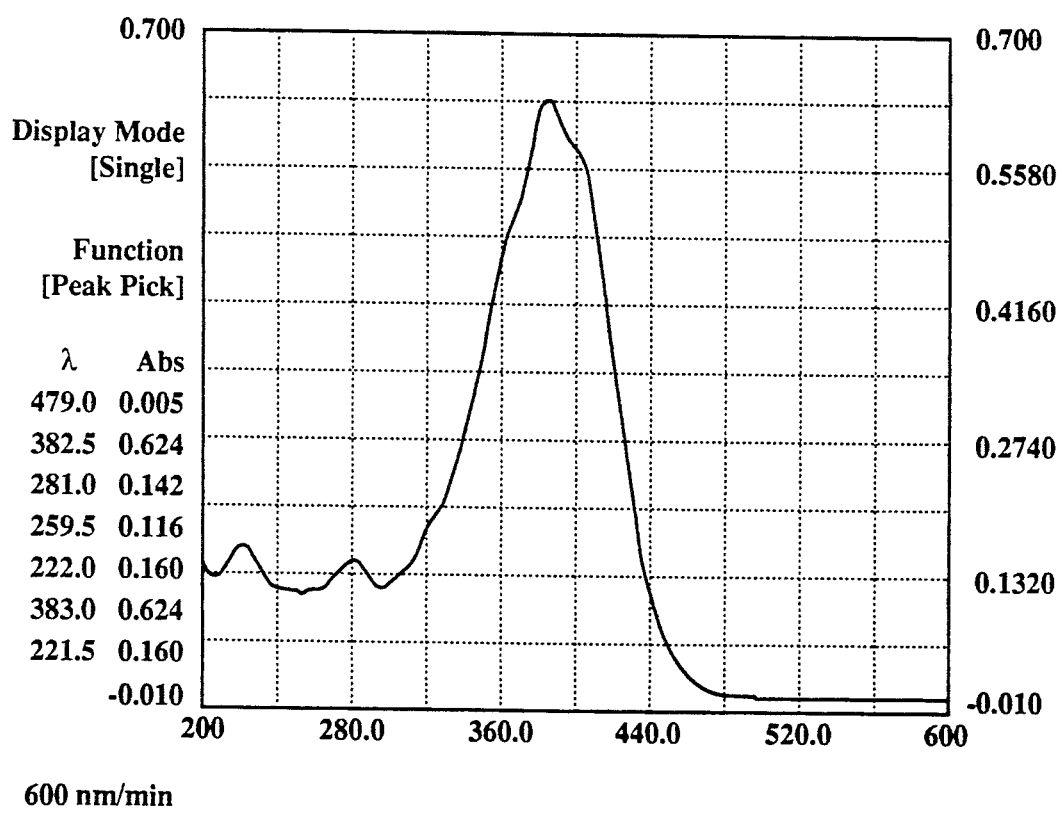
FIG. 3 is a plot of the UV-visible spectrum of dermostatin B in methanol.
Figure 4:
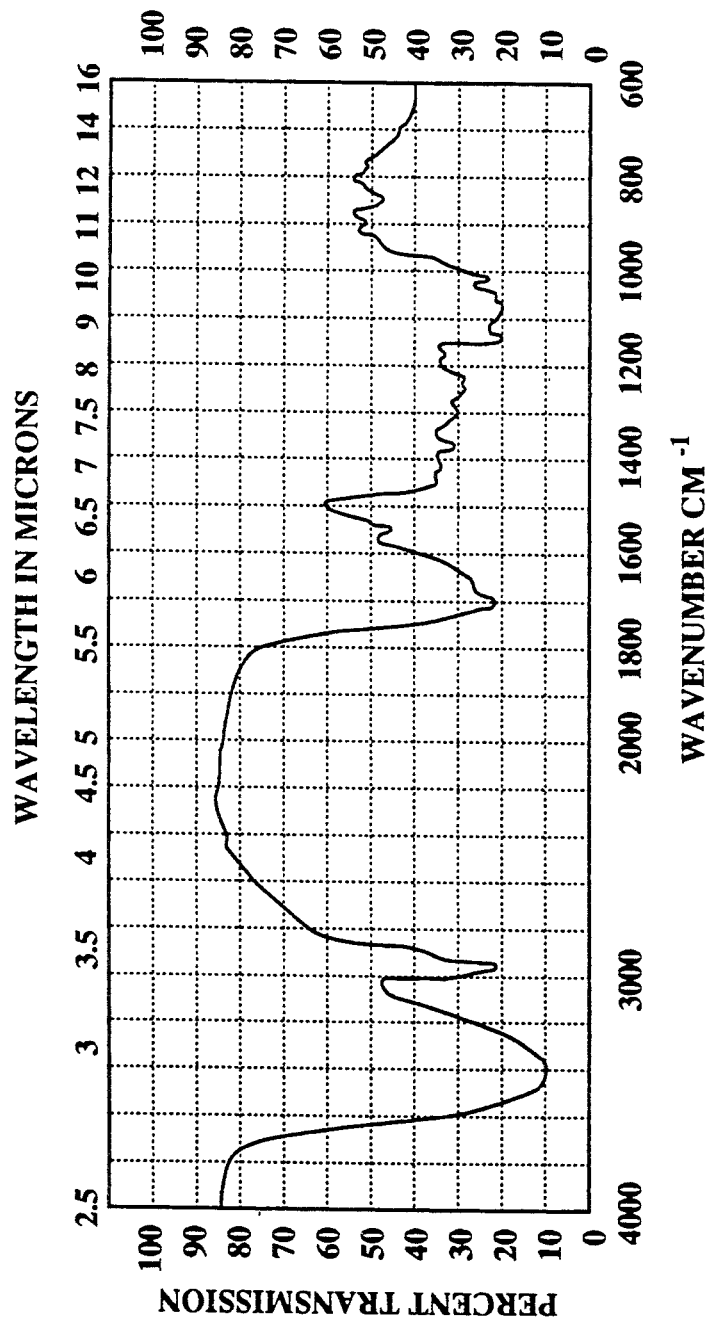
FIG. 4 is a plot of the infrared spectrum for dermostatin complex.
Figure 5:
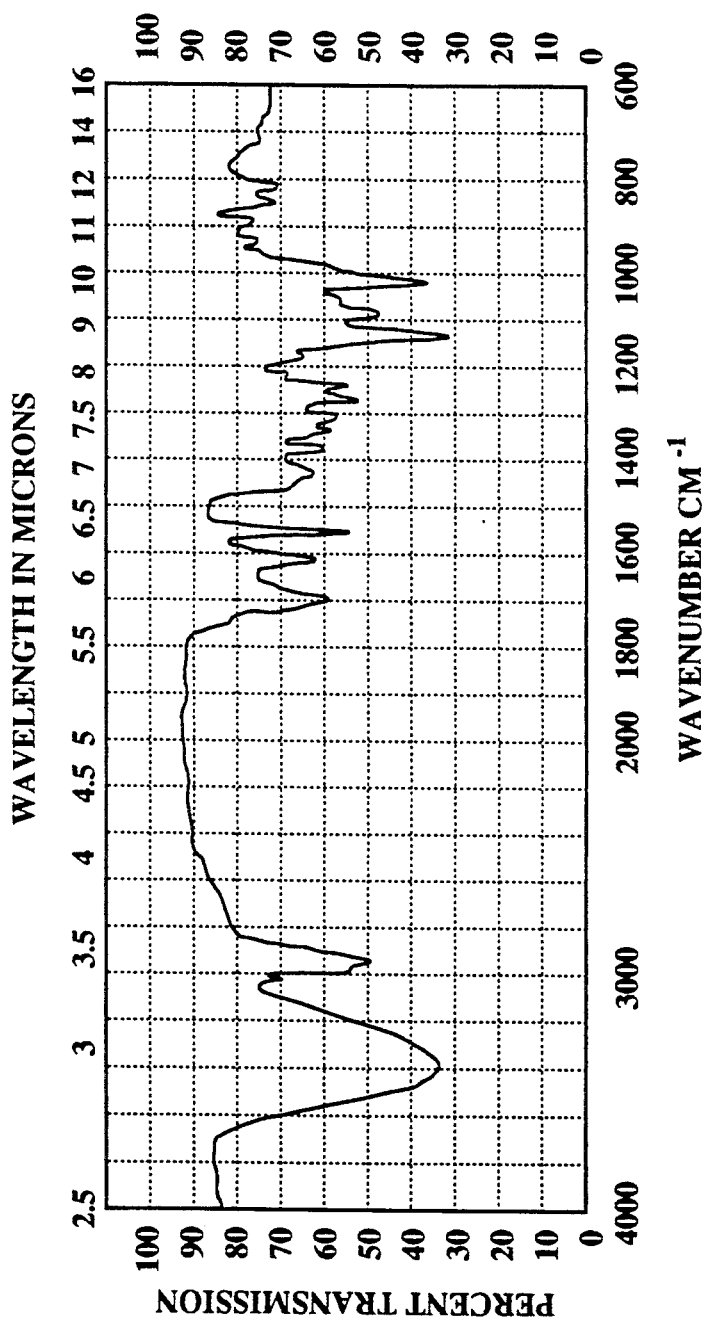
FIG. 5 is a plot of the infrared spectrum for dermostatin A.
Figure 6:
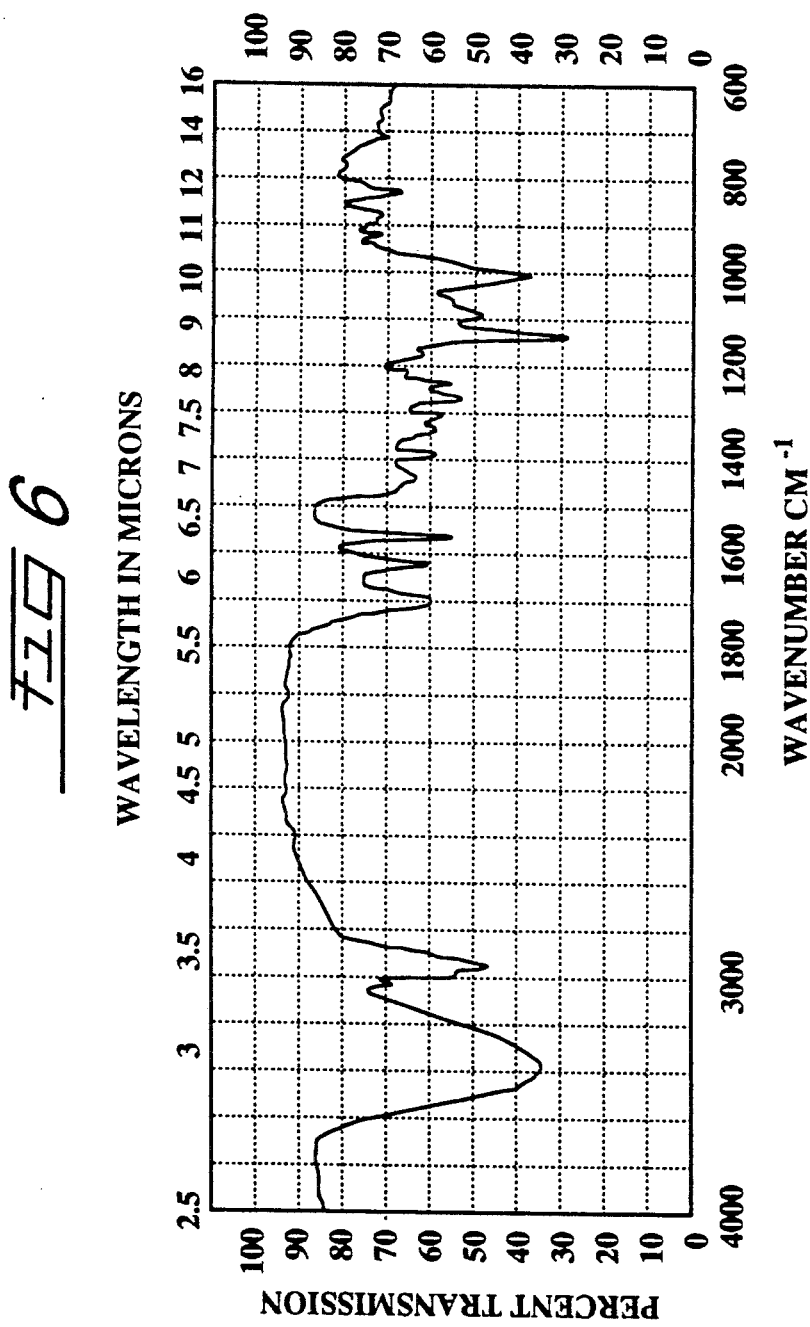
FIG. 6 is a plot of the infrared spectrum for dermostatin B.
Figure 10A:
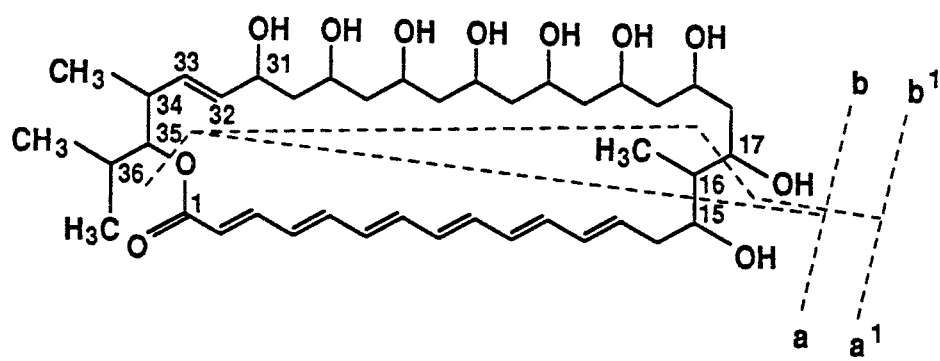
FIG. 10 is a thermospray negative ion mass spectrum for dermostatin A.
Figure 11A:
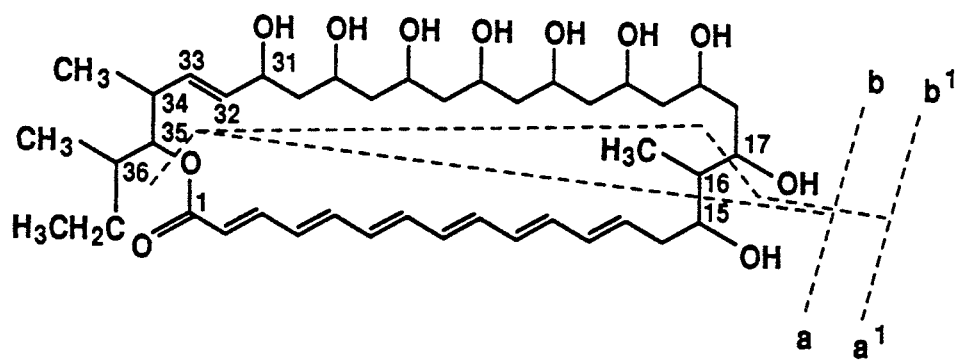
FIG. 11 is a thermospray negative ion mass spectrum for dermostatin B.
Figure 10B:
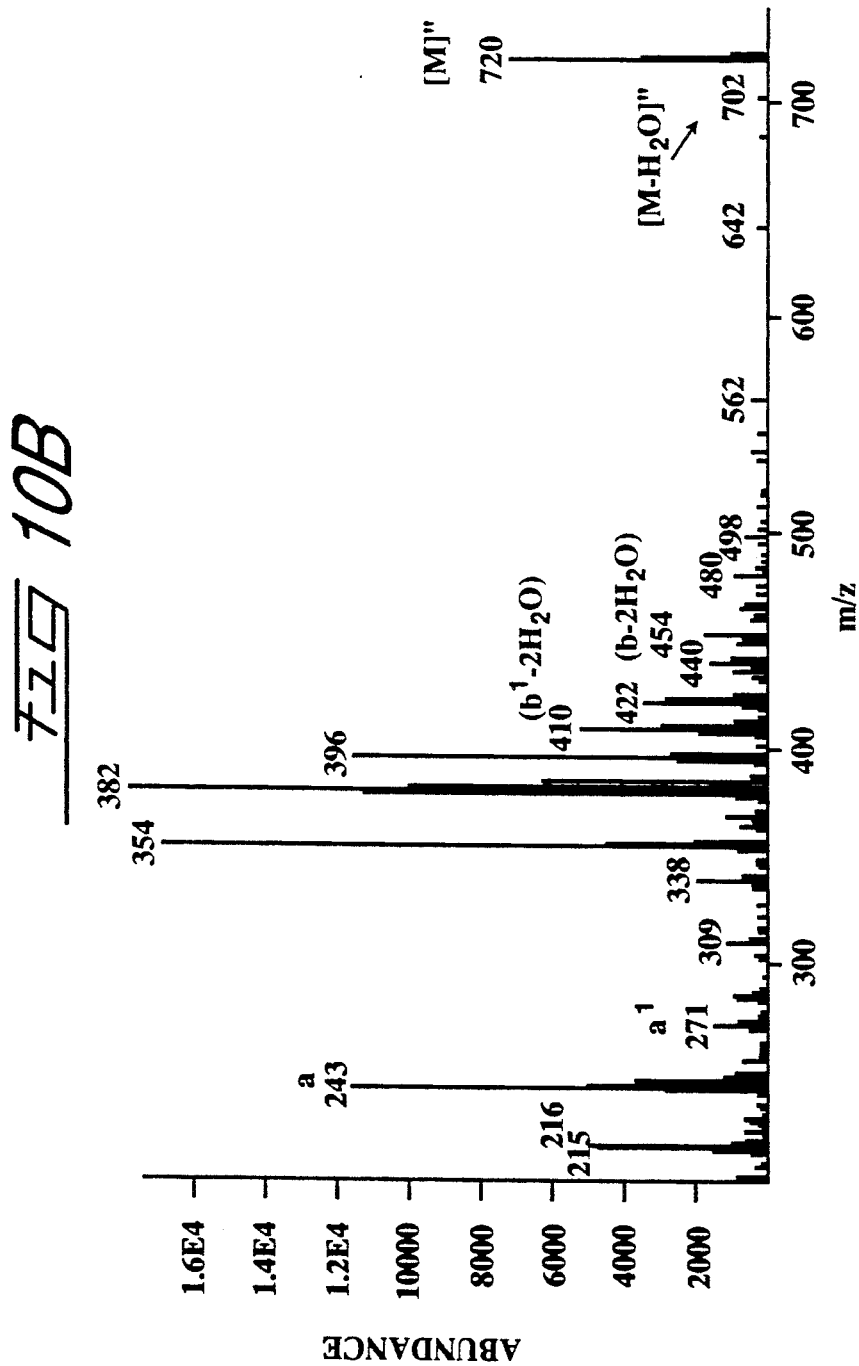

The properties of dermostatin complex, dermostatin A and dermostatin B are summarized in Tables I–III, their respective uv-vis spectra are shown in FIGS. I–III, their respective IR spectra are shown in FIGS. 4–6 and their respective HPLC plots are shown in FIGS. 7–9. The respective thermospray negative ion mass spectra are shown in FIGS. 10–11, for dermostatin A and dermostatin B and their respective structures are shown in FIGS. 12 and 13.

The dermostatin A and dermostatin B recovered by virtue of the above-mentioned separation procedure has a purity of at least about 90 percent, preferable at least about 95% and most preferably at last about 99 percent. The purified product can be dissolved in any pharmaceutically acceptable carrier, such as water, saline solution, or dextrose solution (5%).

As indicated, it has now been found that dermostatin complex, dermostatin A, dermostatin B and their derivatives, including their pharmaceutically acceptable esters, salts and complexes of each, are effective in the treatment of acquired immune deficiency syndrome. The exact mechanism by which these polyene macrolide antibiotics achieve the desired results is not known. It is possible that they reduce the ability of the HIV virus to penetrate the cell walls. However, it is believed that such antibiotics are effective in treating AIDS principally by preventing replication of the virus within the cells, while also decreasing the cytotoxic effects of the virus.

Thus, it is believed that cells susceptible to the HIV virus in the presence of dermostatin A and dermostatin B (separated as most of a complex) would be penetrated by the virus and the target cells would express its reverse transcriptase, while the cell remains viable. However, the ability of dermostatin A and dermostatin B to inhibit or prevent the replication of the virus is demonstrated by the inhibition of the cells in expressing the p24 and p17 virus antigens. These antifungal antibiotics thus prevent the replication of the HIV within target cells and increase the viability of the cells following penetration of the cell by the virus.

The specific results obtained so far have demonstrated that either any of these two antibiotics when simultaneously administered in vitro with the retrovirus found to be responsible for acquired immunodeficiency syndrome (HIV) has increased the viability of cells which are susceptible to that virus and decreased the expression of the viral antigens, p24 and p17.

Because patients suffering from AIDS are susceptible to many opportunistic infections which include fungal infections, AIDS patients have heretofore been administered antifungal antibiotics, such as amphotericin B, for the purpose of attempting to treat various opportunistic fungal infections. In one instance it has been suggested previously that amphotericin B, or other polyene macrolide antibiotics, might be effective in treating the cause of the immune deficiency brought on by the HIV virus, as opposed to treating the secondary opportunistic fungal infections.

The present discovery of the anti-retroviral effects of dermostatin A and dermostatin B with respect to HIV, stands to contribute substantially to understanding the etiology and treatment of AIDS. As previously indicated, these antibiotics are polyene macrolide compounds having antifungal properties. They are produced by cultivation of organisms and extracted from the culture. A general discussion of macrolide antibiotics is found in Kirk-Othmer, Encyclopedia of Chemical Technology, Second Edition, Volume 12, pp. 632 et seq., while ageneral discussion of polyene antibiotics is found in the same work, Volume 16, pp. 133 et seq.

The anti-retroviral agents useful in the present invention include not only dermostatin A and dermostatin B (separate in combination or as dermostatin complex), per se, but also their pharmaceutically acceptable esters, and salts and complexes of both.

The antibiotics, as stated previously, for optimum potential for success, should be administered to the patient in which HIV has been determined to be present, at the earliest possible time. Thus, they should preferably be administered to the patient before the patient has shown any evidence of physiological manifestations of acquired immunodeficiency, preferably before the onset of increased production of antibodies to the HIV virus. From a practical standpoint, after detection of the presence of the HIV retrovirus in a patient, the antibiotics of the present invention should be administered as soon thereafter as possible. Thus, the antibiotics should be administered to the patient before the onset of any opportunistic infections. Should the antibiotics be administered after the patient has developed advanced symptoms of AIDS, typically through the onset of virtually uncontrollable opportunistic infections, the administration of the antibiotics is of little value to eradication of the AIDS virus.

The amount of antibiotic administered should be sufficient to improve the viability of the susceptible lymphocyte cells in the host which are in the presence of the HIV virus. Thus, the antibiotics should be administered at a level such that the concentration of said antibiotics in the environment surrounding the susceptible cells is sufficient to reduce cell death in the presence of the HIV. In in vitro studies, a concentration from about 1 to about 40 ug/ml has been found to be effective in the case of dermostatin A and dermostatin B.

From a physiological standpoint, the amount of antibiotic administered should be sufficient to substantially eliminate the expression of the p24 and p17 antigens from the lymphocyte cells within the patient which have been infected with the HIV virus. Thus, the amount of antibiotic administered should be sufficient to cause the expression of p24 and p17 antigens from the lymphocyte cells to be reduced to normal background levels. A patient receiving an adequate treatment of these antibiotics would ultimately show essentially an absence of p24 and p17 antigens.

The exact amount of dermostatin A or dermostatin B which will be effective for any individual patient may vary over wide ranges. However, as a practical matter, it is believed that administration of from about 5 to about 10 mg of antibiotic per kilogram of body weight on a weekly basis should be sufficient to achieve the desired concentration of antibiotic. The treatment of the patient with the dermostatin A or dermostatin B should continue for a sufficient period of time to insure that the HIV virus is no longer viable within the patient. It is difficult to set forth an exact period within which the therapy should be completed. It is anticipated that the administration of the antibiotic should be necessary only for a period of about 8 weeks. However, the exact timing of the therapy will doubtlessly vary from patient to patient and it will be necessary to treat each patient on an individual basis and to continue each patient's therapy as indicated until there is no possibility that the HIV virus remains viable within that patient. The presence of the HIV virus may be detected by any suitable means known in the art.

Dermostatin A and dermostatin B may be administered to the patient in any suitable form. It will be appreciated by those skilled in the art that other generally accepted delivery methods or forms have the potential of being similarly efficacious, such as emulsions, liposomal encapsulated formulations, various oral dosage forms, attachment of the drug to monoclonal antibodies specific to certain target antigens, metal complexes or chelates, or pro-drugs which generate the active compound in vivo. The exact manner by which the antibiotic is administered to the patient is not critical, so long as the desired concentration of the antibiotic is achieved. In some instances, it may be possible to develop controlled release formulations of antibiotic which will maintain the desired concentration of antibiotic within the patient over prolonged periods of time. Such devices may include implants, transdermal patches, and the like. The exact manner of administration is not critical.

As indicated previously, dermostatin A and dermostatin B are members of a class of compounds described as polyene macrolide antifungal antibiotics. Such polyene macrolides are known to react with sterols, which may be the mechanism through which their antiviral activity is achieved with respect to lipid-enveloped viruses. It is not known whether that mechanism or a totally different mechanism is the basis for the utility of these antibiotics in treating AIDS. Clearly, not all polyene macrolides that have the ability to bind to sterols are therapeutically useful in the treatment of AIDS. It has now been shown that filipin and fungichroin are not active against HIV whereas aromatic polyenes, such as candicidin are toxic to the cells. It is thus clear from this work that only certain groups of polyene macrolides are effective. The extent of the AIDS problem and the lack of an adequate solution to date alone demonstrate the lack of any obvious cure or treatment for AIDS.

Thus, although other possible agents, including other polyene macrolides may be useful in preventing the replication of the HIV virus or otherwise inhibiting its infectivity, the direct adverse effect of such agents upon the cells themselves may make them useless for such treatment. Therefore, although candicidin may be useful to a degree in inhibiting the replication or infectivity of HIV virus, that ability is not present at noncytotoxic levels. When noncytotoxic doses are employed against HIV infection, no advantage whatsoever is seen. When the dosage level of the candicidin is further increased, its own cytotoxic effects takes its toll on the target cells, thus rendering it useless as a treatment for AIDS.

The present invention will be further demonstrated by means of the following non-limiting examples.

EXAMPLES

Example 1

Separation and Purification of Dermostatin A and Dermostatin B from Dermostatin Complex Dermostatin complex was dissolved in dimethylsulfoxide (DMSO) at a concentration of 20 mg dermostatin per milliliter of DMSO. The solution was then injected, 5 ml at a time, through a solvent line into a Waters Delta Pak $C_{18}$ column (19×300 mm, 100 angstrom, 15 micron particle size), using an isocratic solvent system of methanol-water (74:26) as the mobile phase at a flow rate of 14 ml per minute. Chart sensitivity was adjusted to 1.0 AUFS and chart speed to 0.25 cm/minute. The detection for the elution of each component was followed at 390 nm and as the peak was detected, 50 ml fractions were collected. The fractions were checked by analytical HPLC on a Waters Nova Pak $C_{18}$ column (3.9×150 mm, using methanol-water (74:26) as the mobile phase at a flow rate of 1.5 ml/min, and an injection volume of 10 microliters, with detection at UV-Vis, 390 nm. The fractions having a retention time of 9.92 minutes were determined to be the dermostatin A fraction and the fractions having a retention time of 14.36 minutes were determined to be the dermostatin B fraction. The fractions with identical retention times were then combined and each concentrated by rotary evaporation at about 30 degrees C., to a small volume of approximately 5 ml. and the resulting precipitate filtered and dried to form a golden yellow amorphous powder.

The dermostatin A fractions which eluted at 9.92 minutes had a melting point of 135-139 degrees C. and the dermostatin B fractions which eluted at 14.36 minutes had a melting point of 138-144 degrees C. Further analytical information regarding the original dermostatin complex and the purified compounds is set forth in Tables I-III and FIGS. 1-11.

EXAMPLES 2-5 AND COMPARATIVE EXAMPLES A-AR

In Vitro Testing Against HIV

In these examples the dermostatin A and dermostatin B used was purified by the preparative high performance liquid chromatography procedure of Example 1 and had the properties summarized in Tables 2 and 3. Stock solutions (1 mg/ml) were prepared in dimethyl sulfoxide (DMSO) and subsequent dilutions to the required concentrations were made in the culture medium. The dermostatin A and dermostatin B formulations were tested for activity against HIV virus in H9 cells in log phase. The virus was prepared from HIV infected H9 cells in culture. H9 is a transformed human lymphocyte cell line that is permissive for HIV. These cells are maintained by serial passage in culture, using medium containing RPMI-1640 supplemented with 20% fetal bovine serum, 2% glutamine and 1% gentamicin. Cells were harvested in log phase, and approximately $4\times10^5$ cells were added per ml of test culture.

Stock virus was obtained from HIV infected H9 cells in culture. The cells were harvested by centrifugation and the virus was isolated from the conditioned media by twice banding on sucrose gradient. The virus band sedimented at a density of 1.16-1.19 g/ml and was collected, pelleted by centrifugation, and resuspended in TNE (10 mM Tris.HCl, pH 7.5, 0.1M NaCl, 0.001M EDTA) at $2\times1011$ virus particles per ml.

Infection of the H9 cells by the virus was accomplished by pretreating the cells with 2 μg/ml Polybrene (1,5 dimethyl-1,5 diazaundecamethylenepolymethobromide [Sigma]) and adding $2\times10^7$ virus particles/ml culture, concurrently with the antibiotic formulations, as discussed below, except in the case of the controls. The cultures were incubated for four days at 37 degrees C. in a humidified atmosphere containing 5% $CO_2$. The cells in each culture were dispersed in the medium by trituration and an aliquot was analyzed for cell viability. Cells excluding trypan blue dye were considered viable. The remaining portion of each culture was used to determine expression of the HIV antigens, p24 and p17.

The expression of the HIV antigens, p24 and p17, was determined through the use of immunofluorescence assays which were carried out on methanol-acetone fixed cells using monoclonal antibodies for HIV protein antigens, p17 and p24. After removal of the aliquot of cell culture for determination of cell number and viability as discussed above, the remaining cultures were centrifuged to separate the cells. The cells were resuspended in phosphate-buffered saline (PBS) to about $1\times10^6$/ml and 10-50 ul were added to each well of an 8-well toxoplasmosis slide for immunofluorescence studies. The slides were air-dried for one hour, fixed in methanol-acetone (1:1,v/v) for 15 minutes at room temperature and subsequently air-dried for 10 minutes. The fixed cells were pretreated with 10% normal goat serum for 30 to 45 minutes at 37 degrees C. in a moist chamber to preclude the non-specific absorption of FIC-goat anti-mouse IgG to be added later, after which the slides were rinsed three to four times in PBS for 15 minutes each time. The mouse monoclonal antibodies to HIV antigens, p24 and p17, were added to duplicate wells, incubated at room temperature in a humid chamber for one hour and washed with PBS containing 0.25% Triton X-100 for two hours.

The cells were subsequently exposed to fluorescein (FITC)-labeled goat anti-mouse IgG (Cappel Labs) for one hour and washed overnight with PBS containing 0.25% Triton X-100. The slides were mounted with 50% glycerol and the cell fluorescence was observed under a fluorescence microscope. The number of fluorescence-positive cells in several fields were counted and reported as a percent of total cells within those fields. The activity of dermostatin A and dermostatin B against HIV was tested by adding varying concentrations of the drug as shown in the following Tables, simultaneously with virus to H9 cells. After 4 days the cells were harvested and the number of viable cells determined (impermeable to trypan blue). In the Tables, the drug "dermostatin" is the normal dermostatin complex which is a mixture containing both dermostatin A and dermostatin B.

Examples 2-5 employ dermostatin A at a concentration from 0.01-5 micrograms per liter and Examples 6-9 show the effects of dermostatin B at similar concentrations. Those examples were compared to comparative examples A - D which used amphotericin B as the anti- HIV agent, comparative examples E-H which used nystatin as the anti-HIV agent and comparative examples I-L which used amphotericin A as the anti-HIV agent. The results of that comparative study are set forth in Table IV.

In Examples 10-21, dermostatin complex at concentrations from 5-40 micrograms per ml is compared to dermostatin A employed at concentrations from 0.01-5.0 micrograms per milliliter, and with dermostatin B employed at similar concentrations. The results of those comparisons are set forth in Table V.

Examples 22-25 employ dermostatin complex at concentrations from 5-15 micrograms per milliliter and are compared to other known antifungal agents, mycoticin (comparative examples M-P) and faeriefungin (comparative examples Q-T). The results of those comparisons are set forth in Table VI.

Comparative examples U-W and X-Z, respectively, show the activity of filipin and lagosin as anti-HIV agents. The results of those comparisons are set forth in Table VII. Likewise, the activity of several known antifungal agents, other than dermostatin, is compared in Table VIII wherein mycoticin (comparative examples AA-AC), mycoticin A (comparative examples AD-AF), mycoticin B (comparative examples AG-AI), faeriefungin (comparative examples AJ-AL), faeriefungin A (comparative examples AM-AO), and faeriefungin B (comparative examples AP-AR) are set forth. Dermostatin complex and dermostatin A and dermostatin B showed significant anti-HIV activity from 1 μg/ml through 40 μg/ml. The cell viability results are contained in Tables IV-VI.

Of particular importance is the pronounced effect which the dermostatin A and dermostatin B had upon the expression of the viral antigens p24 and p17 from the viable cells. In this respect, it was found that by using as little as one microgram per ml of dermostatin A or B, production of antigens p24 and p17 was reduced to 3 to 8%, of the control in which the cells had been exposed to the HIV virus, in the absence of any antibiotic (Table IV). When the concentration of the dermostatins was increased to 5 micrograms per ml, the levels of the antigens p24 and p17 were both reduced to 3-4% of the control values. Thus, the use of the dermostatins demonstrates a dramatic decrease in the expression of the HIV antigens. One set of the data concerning p24 and p17 antigen production is contained in Table IV which also shows significant cell viability results for those antibiotics. A reduction in the production of HIV antigens is a very strong indication that the HIV virus was inhibited from replicating within the infected cells. Thus, not only did these antibiotics provide for increased cell viability in the presence of HIV retrovirus, but they also prevented the virus within the infected cells from replicating.

In Table V, certain comparative data is also set forth for other polyene macrolide antibiotics. Amphotericin A and B as well as nystatin have previously been shown by the inventor of the present application to be useful in the treatment of HIV infection. Table V contains a comparison between the effectiveness of those compounds and the effectiveness of the dermostatins. As can be readily ascertained from that table, the dermostatins at lower concentrations were able to inhibit the expression of the p24 and p17 proteins more so than any of the comparative polyene macrolides, while maintaining superior Cell viability.

In general, Tables IV-VI contain data for dermostatin complex, as well as for dermostatins A and B at various levels of concentration from 0.01 to 40 μg/ml. The data shows that cell viability remains high over the tested range and that at a level of about 1 μg/ml, high levels of inhibition to viral replication have been achieved.

Tables VI-VIII contain comparative data for other macrolide antibiotics. The data shows that none of those other antibiotics demonstrated a meaningful level of viral inhibition, except mycoticin, when compared with dermostatin complex. Table VIII demonstrates, however, that the results of Table VI regarding mycoticin were anomolous and could not be reproduced. In that table, faeriefungin activity is also shown to be relatively high, from the standpoint of viral inhibition. However, although better than mycoticin, the cell viability is still much less than the viability achieved with the dermostatins.

The results of these experiments clearly indicate the protective effect of dermostatin A and dermostatin B on target cells against the cytopathic action of HIV and the superiority of that effect compared to other polyene macrolide antibiotics.

TABLE I

| Physicochemical Properties of Dermostatin Complex | |
|---|---|
| Nature: | Golden yellow amorphous powder |
| Mol. Formula: | $C_{40}H_{64}O_{11}$ (24%; $C_{41}H_{66}O_{11}$ (34%) |
| Mol. Wt: | $C_{40}H_{64}O_{11}$, 720; $C_{41}H_{66}O_{11}$, 734 |
| Melting Point: | 142-146° C. |
| TLC* (Rf): | 0.63 ± 0.02 |
| HPLC** (RT): | $C_{40}H_{64}O_{11}$, 9.92 min; $C_{41}H_{66}O_{11}$, 14.36 min FIG. 7 |
| Solubility: | Soluble in MeOH, DMSO, DMF Insoluble in $H_2O$, pet ether, hexane |
| UV-Vis (MeOH): | FIG. 1 |
| IR (KBr pellet): | FIG. 4 |

*Plates: Silica Gel 60, F254 (20 × 20 cm, 250 thickness); Solvent System: n-Butanol-Acetic Acid-Water (4:1:5, upper layer)
**Column: Nova Pak $C_{18}$ (3.9 × 150 mm); Solvent System: Methanol-Water (74:26); Flow Rate: 1.5 ml/min; Detection: 390 nm

TABLE II

| Physicochemical Properties of Dermostatin A | |
|---|---|
| Nature: | Golden yellow amorphous powder |
| Mol. Formula: | $C_{40}H_{64}O_{11}$ |
| Mol. Wt: | 720 |
| Melting Point: | 135-139° C. |
| TLC* (Rf): | 0.63 ± 0.02 |
| HPLC** (RT): | 9.92 min FIG. 8 |
| Solubility: | Soluble in MeOH, DMSO, DMF Insoluble in $H_2O$, pet ether, hexane |
| UV-Vis (MeOH): | λ max (ε) 383.0 (47,406); 81.0 nm (8,075) FIG. 2 |
| IR (KBr pellet): | FIG. 5 |

*Plates: Silica Gel 60, F254 (20 × 20 cm, 250 thickness); Solvent System: n-Butanol-Acetic Acid-Water (4:1:5, upper layer)
**Column: Nova Pak $C_{18}$ (3.9 × 150 mm); Solvent System: Methanol-Water (74:26); Flow Rate: 1.5 ml/min; Detection: 390 nm

TABLE III

| Physicochemical Properties of Dermostatin B | |
|---|---|
| Nature: | Golden yellow amorphous powder |
| Mol. Formula: | $C_{40}H_{64}O_{11}$ |
| Mol. Wt: | 734 |
| Melting Point: | 138-144° C. |
| TLC* (Rf): | 0.64 ± 0.02 |
| HPLC** (RT): | 14.36 min FIG. 9 |
| Solubility: | Soluble in MeOH, DMSO, DMF Insoluble in $H_2O$, pet ether, hexane |
| UV-Vis (MeOH): | λ max (ε) 383.0 (19,859); 281.0 nm (4,519) FIG. 3 |

TABLE III-continued

Physicochemical Properties of Dermostatin B

| IR (KBr pellet): | FIG. 6 |
|---|---|

*Plates: Silica Gel 60, F254 (20 × 20 cm, 250 thickness); Solvent System: n-Butanol-Acetic Acid-Water (4:1:5, upper layer)
**Column: Nova Pak $C_{18}$ (3.9 × 150 mm); Solvent System: Methanol-Water (74:26); Flow Rate: 1.5 ml/min; Detection: 390 nm

TABLE IV

Comparision of polyene macrolide antibiotics for anti-HIV activity

| Antibiotic | Conc. (g/ml) | Cell Survival (% Control) | % Viral Activity | | |
|---|---|---|---|---|---|
| | | | RT | p24 | p17 |
| Control | 0.1 | 100 | 100 | 100 | 100 |
| Comparative | 10 | 73 | 40 | 8 | 8 |
| Examples A-D | 1.0 | 33 | 48 | 28 | 24 |
| (Amphotericin B) | 0.1 | 11 | 100 | 88 | 96 |
| | 0.01 | 13 | 100 | 100 | 100 |
| Comparative | 10 | 110 | 47 | 3.6 | 1.2 |
| Examples E-H | 1.0 | 83 | 84 | 36 | 25 |
| (Nystatin) | 0.1 | 58 | 86 | 21 | 31 |
| | 0.01 | 49 | 87 | 21 | 31 |
| Examples 2-5 | 5 | 99 | 9 | 3 | 4 |
| (Dermostatin A) | 1 | 92 | 21 | 3 | 4 |
| | 0.1 | 18 | 80 | 100 | 100 |
| | 0.01 | 0 | 100 | 100 | 100 |
| Examples 6-9 | 5 | 97 | 13 | 3 | 4 |
| (Dermostatin B) | 1 | 87 | 25 | 4 | 8 |
| | 0.1 | 0 | 92 | 90 | 80 |
| | 0.01 | 0 | 100 | 100 | 100 |
| Comparative | 10 | 88 | 55 | 19 | 14 |
| Examples I-L | | 75 | 78 | 36 | 37 |
| (Amphotericin A) | 0.1 | 80 | 92 | 44 | 21 |
| | 0.01 | 62 | 84 | 36 | 50 |

Added to cultures of H9 cells (polybrene treated) simultaneously with HIV. After 4 days in culture, surviving viable cells were harvested, counted and examined for expression of virus proteins p24 and p17. The culture supernatants of HIV-infected H9 cells were assayed for reverse transcriptase activity (RT = Reverse Transcriptase).

TABLE V

Effect of Dermostatins on HIV-1 Replication in Cell Culture

| Antibiotic | Conc. (μg/ml) | Cell Survival (% Control) | % Inhibition | | |
|---|---|---|---|---|---|
| | | | RT | p24 | p17 |
| Examples 10-13 | 5 | 22 | 0 | 17 | 8 |
| (Dermostatin) | 10 | 79 | 72 | 93 | 96 |
| | 20 | 94 | 85 | 93 | 96 |
| | 40 | 99 | 91 | 97 | 96 |
| Examples 14-17 | 0.01 | 0 | 0 | 0 | 0 |
| (Dermostatin A) | 0.1 | 18 | 20 | 0 | 0 |
| | 1.0 | 92 | 79 | 97 | 96 |
| | 5.0 | 99 | 91 | 97 | 96 |
| Examples 18-21 | 0.01 | 0 | 0 | 0 | 0 |
| (Dermostatin B) | 0.1 | 0 | 8 | 10 | 20 |
| | 1.0 | 87 | 75 | 96 | 92 |
| | 5.0 | 97 | 87 | 97 | 96 |

TABLE VI

Comparision of Pentaene and Hexaene Macrolides for Anti-HIV Activity

| Antibiotic Tested | Conc. (g/ml) | % Inhibition | | |
|---|---|---|---|---|
| | | RT | p24 | p17 |
| Comparative | 5 | 4 | 0 | 0 |
| Examples M-P | 7 | 26 | 35 | 22 |
| (Mycoticin) | 10 | 54 | 45 | 44 |
| | 15 | 90 | 95 | 95 |
| Comparative | 5 | 0 | 0 | 0 |
| Examples Q-T | 7 | 0 | 0 | 0 |
| (Faeriefungin) | 10 | 60 | 45 | 40 |
| | 15 | Toxic | Toxic | Toxic |
| Examples 22-25 | 5 | 10 | 0 | 0 |
| (Dermostatin) | 7 | 44 | 55 | 50 |
| | 10 | 75 | 85 | 78 |
| | 15 | 85 | 95 | 89 |

TABLE VII

Comparative Examples Comparision of Filipin and Lagosin on HIV Replication in Cell Culture

| Antibiotic | Conc. (g/ml) | Cell Survival (% Control) | % Inhibition | | |
|---|---|---|---|---|---|
| | | | RT | p24 | p17 |
| Comparative | 0.1 | 48 | 14 | 0 | 33 |
| Examples U-W | 1.0 | 51 | 0 | 55 | 50 |
| (Filipin) | 10.0 | 49 | 12 | 0 | 0 |
| Comparative | 0.1 | 48 | 0 | 0 | 17 |
| Examples X-Z | 1.0 | 38 | 0 | 27 | 0 |
| (Lagosin) | 10.0 | 26 | 16 | 37 | 17 |

TABLE VIII

Comparative Examples Effect of Mycoticins and Faeriefungins on HIV Replication in Cell Culture

| Antibiotic | Conc. (g/ml) | Cell Survival (% Control) | % Inhibition | | |
|---|---|---|---|---|---|
| | | | RT | p24 | p17 |
| Comparative | 5 | 0 | 30 | 8 | 0 |
| Examples AA-AC | 10 | 0 | 0 | 0 | 0 |
| (Mycoticin) | 20 | 0 | 0 | 0 | 0 |
| Comparative | 5 | 0 | 0 | 23 | 16 |
| Examples AD-AF | 10 | 4 | 11 | 25 | 26 |
| (Mycoticin A) | 20 | 14 | 19 | 37 | 28 |
| Comparative | 5 | 0 | 7 | 0 | 0 |
| Examples AG-AI | 10 | 10 | 11 | 25 | 19 |
| (Mycoticin B) | 20 | 15 | 67 | 38 | 33 |
| Comparative | 5 | 0 | 19 | 0 | 0 |
| Examples AJ-AL | 10 | 0 | 59 | 0 | 0 |
| (Faeriefungin) | 20 | 62 | 92 | 68 | 74 |
| Comparative | 5 | 0 | 40 | 20 | 15 |
| Examples AM-AO | 10 | 0 | 11 | 0 | 0 |
| (Faeriefungin A) | 20 | 0 | 0 | 0 | 0 |
| Comparative | 5 | 0 | 12 | 0 | 0 |
| Examples AP-AR | 10 | 12 | 73 | 45 | 43 |
| (Faeriefungin B) | 20 | T | T | T | T |

I claim:

1. A method for producing substantially pure dermostatin A and dermostatin B comprising dissolving dermostatin complex in dimethylsulfoxide at a concentration from about 1 to about 100 mg of dermostatin per milliliter of dimethylsulfoxide; injecting the solution into a suitable separation column, using an isocratic solvent system of methanol and water as the mobile phase at a flow rate of from about 10 to about 20 ml per minute; detecting the absorption of the effluent at 390 nm and as a fraction having absorption at 390 nm is detected, recovering said fraction; combining the fractions with identical retention times; concentrating the combined fractions; and recovering the resultant precipitate.

* * * * *